(12) United States Patent
Gu et al.

(10) Patent No.: US 10,647,669 B2
(45) Date of Patent: May 12, 2020

(54) COMPOSITION CONTAINING LUTEIN/LUTEIN ESTER AND APPLICATIONS THEREOF

(71) Applicant: SinoNutraceutical Co., Ltd., Pudong New District, Shanghai (CN)

(72) Inventors: Maojian Gu, Shanghai (CN); Jianmei Su, Shanghai (CN)

(73) Assignee: SinoNutraceutical Co., Ltd., Pudong New District, Shanghai (CN)

( * ) Notice: Subject to any disclaimer, the term of this patent is extended or adjusted under 35 U.S.C. 154(b) by 0 days.

(21) Appl. No.: 16/320,712

(22) PCT Filed: Jun. 14, 2017

(86) PCT No.: PCT/CN2017/088229
§ 371 (c)(1),
(2) Date: Jan. 25, 2019

(87) PCT Pub. No.: WO2018/019048
PCT Pub. Date: Feb. 1, 2018

(65) Prior Publication Data
US 2019/0161441 A1 May 30, 2019

(30) Foreign Application Priority Data

Jul. 27, 2016 (CN) .......................... 2016 1 0600364

(51) Int. Cl.
| | | |
|---|---|---|
| A61K 9/20 | (2006.01) | |
| C07C 403/24 | (2006.01) | |
| A61P 27/02 | (2006.01) | |
| A23L 33/105 | (2016.01) | |
| A61K 47/12 | (2006.01) | |
| A61K 31/23 | (2006.01) | |
| A61K 47/02 | (2006.01) | |
| A61K 31/047 | (2006.01) | |
| A61K 31/015 | (2006.01) | |
| A61K 47/40 | (2006.01) | |
| A61K 47/26 | (2006.01) | |
| A61P 27/12 | (2006.01) | |
| A61P 27/10 | (2006.01) | |
| A61K 9/00 | (2006.01) | |

(52) U.S. Cl.
CPC .......... *C07C 403/24* (2013.01); *A23L 33/105* (2016.08); *A61K 9/0056* (2013.01); *A61K 9/20* (2013.01); *A61K 31/015* (2013.01); *A61K 31/047* (2013.01); *A61K 31/23* (2013.01); *A61K 47/02* (2013.01); *A61K 47/12* (2013.01); *A61K 47/26* (2013.01); *A61K 47/40* (2013.01); *A61P 27/02* (2018.01); *A61P 27/10* (2018.01); *A61P 27/12* (2018.01); *A23V 2002/00* (2013.01)

(58) Field of Classification Search
CPC ...................................................... A61K 9/20
See application file for complete search history.

(56) References Cited

U.S. PATENT DOCUMENTS

| | | | | |
|---|---|---|---|---|
| 2007/0110808 A1* | 5/2007 | Bhattacharya | ....... | A61K 9/2081 424/473 |
| 2014/0248369 A1* | 9/2014 | Minatelli | ............. | A61K 31/122 424/522 |

FOREIGN PATENT DOCUMENTS

| | | |
|---|---|---|
| CN | 1452955 A | 11/2003 |
| CN | 1816355 A | 8/2006 |
| CN | 101243875 A | 8/2008 |
| CN | 103735733 A | 4/2014 |
| CN | 103750323 A | 4/2014 |
| CN | 104224890 A | 12/2014 |
| CN | 105077504 A | 11/2015 |
| CN | 106236739 A | 12/2016 |

OTHER PUBLICATIONS

Int'l Search Report dated Sep. 20, 2017 in Int'l Application No. PCT/CN2017/088229.
Office Action dated May 2, 2018 in CN Application No. 201610600364.2.
Office Action dated Oct. 29, 2018 in CN Application No. 201610600364.2.
You, Xin, "Protection Function of Lutein and Lutein Ester on Eyes," Food and Nutrition in China, vol. 21, No. 7, pp. 79-80 (2015) (last page Englich abstract).

* cited by examiner

*Primary Examiner* — Benjamin J Packard
(74) *Attorney, Agent, or Firm* — Ice Miller LLP

(57) ABSTRACT

Disclosed in the present invention are a composition containing lutein/lutein ester and applications thereof. Components of the composition containing lutein/lutein ester comprise lutein/lutein ester, β-carotene and a pharmaceutically acceptable carrier. The weight ratio of lutein/lutein ester to β-carotene is 1:0.1-100. In the present invention, by cooperatively using lutein/lutein ester and β-carotene and using auxiliary natural healthy ingredients, the dosage form of an orally disintegrating tablet is prepared. The orally disintegrating tablet is absorbed through the oral cavity, has fast effectiveness and small first-pass effect, reduces damage of gastric acid to lutein/lutein ester, has high bioavailability, and has the characteristics of nutritional and health-care effects, good mouthfeel and fast absorption. By eating the product, visual power can be obviously enhanced, the ocular blood flow is increased, and eye muscle fatigue is alleviated, and accordingly the morbidities of cataract, senile niacula lutea retinae lesion and adolescent myopia are reduced.

4 Claims, No Drawings

2

COMPOSITION CONTAINING LUTEIN/LUTEIN ESTER AND APPLICATIONS THEREOF

CROSS-REFERENCE TO RELATED APPLICATION

This application is a Section 371 of International Application No. PCT/CN2017/088229, filed Jun. 14, 2017, which was published in the Chinese language on Feb. 1, 2018, under International Publication No. WO 2018/019048 A1, which claims priority under 35 U.S.C. § 119(b) to Chinese Application No. 2016106003642, filed Jul. 27, 2016, the disclosures of which are incorporated herein by reference in their entirety.

TECHNICAL FIELD

The present invention relates to a lutein/lutein ester preparation.

BACKGROUND

In recent years, people's learning, work and entertainment have increasingly relied on video display terminals such as computers, televisions, mobile phones, etc. Frequent overuse of the eye, not paying attention to eye care, would lead to a decreased vision, and even induce a variety of ocular diseases, bringing great pain to people's body and mind.

Lutein ester is a natural antioxidant found in plant cells that is metabolized into lutein in the human body. Lutein is considered to be "the vitamin of the eye" and has a special effect on preventing the incidence of cataracts, senile macular degeneration of retina and the occurrence of adolescent myopia. Lutein also has anti-cancer effect, may prevent the occurrence of cardiovascular diseases, and has health function for enhancing the body's immunity, etc.

At present, there are various health care supplements, effervescent tablets, compressed candy on the market for lutein/lutein ester to relieve visual fatigue. Strong acid has a great destructive effect on the stability of lutein/lutein ester. These products enter the gastrointestinal tract quickly after oral feeding, and the low pH (0.9-1.8) of the gastric juice would greatly reduce the bioavailability of the lutein/lutein ester, which is not mentioned in the prior art.

SUMMARY

It is an object of the present invention to provide a composition containing lutein/lutein ester and the application thereof to overcome the deficiencies in the prior art.

The composition containing lutein/lutein ester according to the invention has a high disintegration rate and rapid absorption, and is absorbed into the blood through the oral mucosa. The composition comprises lutein/lutein ester and beta-carotene and pharmaceutically acceptable carriers, in which the weight ratio of lutein/lutein ester to beta-carotene is 1:0.1-100.

Preferably, the weight ratio of lutein/lutein ester to beta-carotene is 1.5-10:1; most preferably 1.5-4.5:1.

The term "lutein/lutein ester" refers to lutein or lutein ester.

Preferably, the composition containing lutein/lutein ester comprises the following components by weight:

| | |
|---|---|
| lutein ester | 0.5-25% |
| cyclodextrin | 4.5-45% |
| acidity regulator | 3-10% |
| loose agent | 3-15% |
| calcium carbonate | 0-5% |
| lactose | 10-25% |
| maltodextrin | 5-25% |
| alditol | 5-20% |
| beta-carotene | 0.1-25% |
| sugar powder | 5-30% |
| fruit powder | 12-30% |
| magnesium stearate | 0.5-1.5%. |

Preferably, the composition containing lutein/lutein ester comprises the following components by weight:

| | |
|---|---|
| lutein ester | 1.5-2% |
| cyclodextrin | 9-10% |
| acidity regulator | 5-6% |
| loose agent | 7-8% |
| calcium carbonate | 0-1% |
| lactose | 13-15% |
| maltodextrin | 12-15% |
| alditol | 10-14% |
| beta-carotene | 1-2% |
| sugar powder | 14-15% |
| fruit powder | 17-22% |
| magnesium stearate | 1-1.5%. |

Wherein the content of the beta-carotene is any percentage between 0.1% and 25%, such as 1%, 2%, etc.

The acidity regulator is one or more selected from the group consisting of citric acid, malic acid, fumaric acid, lactic acid, tartaric acid, and the like;

the loose agent is one or more selected from the group consisting of soda, baking soda, calcium carbonate, magnesium carbonate, and the like;

the sugar powder is one or more selected from the group consisting of white granulated sugar powder, fructose powder and glucose powder;

the fruit powder is one or more of the darker fruit powders selected from the group consisting of blueberry powder, black currant powder, cranberry powder, tomato powder, grape powder, mulberry powder, and the like;

the alditol is one or more selected from the group consisting of sorbitol, mannitol, xylitol, and erythritol.

The preparation process of the present invention is conventional. Each of the components is mixed, and then prepared into an orally disintegrating tablet, powder or capsule by the method known in the art.

Clinical observations show that the composition containing lutein/lutein ester of the present invention has significant health and therapeutic effects on various ocular diseases, and particularly, has a special effect for preventing the incidence of cataract, senile macular degeneration of retina and the occurrence of juvenile myopia.

Therefore, the composition containing lutein/lutein ester can be used for the manufacture of a medicament for treating ocular diseases, or for the manufacture of an ocular health care supplement.

The ocular diseases comprise dizziness, eye pain, weak dark adaptation, blurred vision, photophobia, dry eyes, blink, myopia, macular degeneration of retina or the like.

Generally, the dosage of the composition containing lutein/lutein ester is 1-2 g/day;

The beneficial effects of the invention are:

Lutein/lutein ester and beta-carotene are applied in synergism, together with natural health ingredients, to form a dosage form of orally disintegrating tablets. The dosage form is orally absorbed, has quick onset effect, small first pass effect and high bioavailability, such that the dosage form has the characteristics of nutritional and health-care effects, as well as good monthfeel and fast absorption. Visual ability may be developed, eyeball blood flow may be increased, and fatigue of eye muscle may be alleviated by having the product, and incidence of cataracts, senile macular degeneration of retina and adolescent myopia would be decreased.

DETAILED DESCRIPTION

Example 1

Formulation: (by Weight)

| | | | |
|---|---|---|---|
| lutein ester | 2% | cyclodextrin | 9% |
| citric acid | 6% | calcium carbonate | 1% |
| lactose | 15% | maltodextrin | 12% |
| xylitol | 14% | beta-carotene | 2% |
| fructose powder | 14% | cranberry fruit powder | 17% |
| magnesium stearate | 1% | sodium bicarbonate | 7% |

Preparation Process:

Each of the components is mixed and then prepared into an orally disintegrating tablet by the method known in the art.

Clinical Observation:

(1) Clinical Data

Clinical trials were performed on 220 outpatients who were not hospitalized and volunteered to participate in the trial with clinical manifestations of dizziness, eye pain, weak dark adaptation, blurred vision, photophobia, dry eyes, blink; wherein 110 patients were arranged in the treatment group (male:female=1:1), and 110 patients were arranged in the control group (male:female=1:1).

(2) Treatment

Zhen Shi Ming eye drops were applied to the control group with once a day and 15 days for a course of treatment; the preparation of the present invention was administrated orally to the treatment group with 550 mg/tablet and 4 tablets a day.

(3) The clinical trial results are recorded as follows:

There is a significant difference between the treatment group and the control group. Therefore, the preparation of the present invention has significant efficacy on clinical application.

Example 2

| | | | |
|---|---|---|---|
| lutein | 1.5% | cyclodextrin | 10% |
| citric acid | 4% | malic acid | 1% |
| sodium carbonate | 1.5% | sodium bicarbonate | 6.5% |
| lactose | 13.0% | maltodextrin | 15% |
| erythritol | 10% | beta-carotene | 1% |
| fructose powder | 15% | blueberry powder | 15% |
| black currant powder | 5% | magnesium stearate | 1.5% |

Clinical Observation:

(1) Clinical Data

Clinical trials were performed on 180 outpatients who were not hospitalized and volunteered to participate in the trial with clinical manifestations of dizziness, eye pain, weak dark adaptation, blurred vision, photophobia, dry eyes, blink; wherein 100 patients were arranged in the treatment group (male:female=1:1), and 80 patients were arranged in the control group (male:female=1:1).

(2) Treatment

Eye drops were applied to the control group with once a day and 15 days for a course of treatment; the preparation of the present invention was administrated orally to the treatment group with 550 mg/tablet and 4 tablets a day.

| | Control group | | | Treatment group | | |
|---|---|---|---|---|---|---|
| Symptom | Before administration | Effective number after administration | Effective rate % | Before administration | Effective number after administration | Effective rate % |
| Dizziness | 15 | 6 | 40 | 18 | 15 | 83 |
| Eye pain | 17 | 6 | 35 | 14 | 12 | 86 |
| Weak dark adaptation | 12 | 4 | 33 | 14 | 13 | 93 |
| Blurred vision | 20 | 9 | 45 | 21 | 18 | 86 |
| Photophobia | 15 | 8 | 53 | 12 | 10 | 83 |
| Dry eyes | 16 | 8 | 50 | 16 | 14 | 88 |
| Blink | 15 | 8 | 53 | 15 | 12 | 80 |

(3) The clinical trial results are recorded as follows:

|  | Control group | | | Treatment group | | |
| --- | --- | --- | --- | --- | --- | --- |
| Symptom | Before administration | Effective number after administration | Effective rate % | Before administration | Effective number after administration | Effective rate % |
| Dizziness | 12 | 6 | 50 | 15 | 13 | 87 |
| Eye pain | 12 | 6 | 50 | 14 | 12 | 86 |
| Weak dark adaptation | 10 | 4 | 40 | 13 | 11 | 85 |
| Blurred vision | 11 | 6 | 55 | 18 | 17 | 94 |
| Photophobia | 15 | 7 | 47 | 12 | 10 | 83 |
| Dry eyes | 10 | 5 | 50 | 15 | 14 | 93 |
| Blink | 10 | 4 | 40 | 13 | 11 | 85 |

There is a significant difference between the treatment group and the control group. Therefore, the preparation of the present invention has significant efficacy on clinical application.

Stability Test

| | | Absorbance values at different time period | | | | | |
| --- | --- | --- | --- | --- | --- | --- | --- |
| Sample | Conditions | 0 h | 1 h | 6 h | 24 h | 72 h | 240 h |
| Example 1 | Illumination | 0.853 | 0.104 | — | — | — | — |
|  | Double aluminum package | 0.853 | 0.849 | 0.850 | 0.847 | 0.853 | 0.855 |
| Example 2 | Illumination | 0.855 | 0.003 | — | — | — | — |
|  | Double aluminum package | 0.855 | 0.855 | 0.852 | 0.850 | 0.843 | 0.845 |

Illumination has a strong destructive effect on the stability of the product, and the product with double aluminum package has good stability.

Effect of pH on the Stability of Lutein/Lutein Ester

The acetone aqueous solutions of lutein and lutein ester with pH 1.5 and pH 3 were prepared respectively, and the absorbance values at different time period are shown as follows:

| | | Absorbance values at different time period | | | | | |
| --- | --- | --- | --- | --- | --- | --- | --- |
| Sample | Conditions | 0 h | 12 h | 24 h | 36 h | 48 h | 96 h |
| Lutein | pH 1.5 | 0.843 | 0.559 | 0.452 | 0.368 | 0.267 | 0.151 |
|  | pH 3.0 | 0.845 | 0.566 | 0.495 | 0.428 | 0.341 | 0.268 |
| Lutein ester | pH 1.5 | 0.844 | 0.588 | 0.466 | 0.377 | 0.259 | 0.155 |
|  | pH 3.0 | 0.837 | 0.597 | 0.502 | 0.439 | 0.356 | 0.274 |

The above data shows that absorbance values of lutein ester and lutein decrease significantly under strong acid conditions. The retention of lutein ester is 18.36% and of lutein is 17.80% after placing for 96 h at pH 1.5.

Animal Experiment

1. Purpose of the Test

Comparison and evaluation of pharmacokinetic properties of rats after oral and intragastric administration of the preparation of the examples under fasting conditions 2. Test Method 2.1 Test Drugs Preparation for the Test: Example 2;

Dosage for the administration of the preparation: Lutein concentration 10 mg/kg 2.2 Test Animals Male SD rats, 7-8 weeks old, weighing 180-220 g, were provided by the Animal Testing Center of Shanghai Institute of Materia Medica with the license number SYXK (Hu) 2010-0049. Adaptive feeding was performed on the tested animals at the test site for 3-7 days before the test day.

2.3 Test Design

16 SD rats, male, were randomly divided into 4 groups, with 4 in each group. Each of the preparations was administrated orally and intragastricly respectively, and the specific arrangement is shown in Table 1 below:

TABLE 1

| Test group table | | | | | |
| --- | --- | --- | --- | --- | --- |
| Group | Number of the animal | Administrated preparation | Dosage of the administration (mg/kg) | Fasting or not | Manner of administration |
| 1 | 4 | Test preparation | 10 | Fasting | Oral |
| 2 | 4 | Test preparation | 10 | Fasting | Intragastric |

Fasting was performed for 12 h before administration with free drinking of water. Food was provided uniformly at 2 h after administration.

2.4 Time Point for Blood Collection and Sample Processing:

0.25, 0.5, 1.0, 2.0, 3.0, 5.0, 7.0, 10 and 24 h after administration;

At the above set time points, 0.2 ml of venous blood was taken from the posterior venous plexus of the rat eyeball, and placed in a heparinized tube. Centrifugation was performed at 11,000 rpm for 5 min to separate the plasma. Freezing was conducted in a refrigerator at −20° C.

2.5 Sample Detection

The concentration of lutein in plasma was determined by LC-MS/MS, the linear range in the analytical method was 3.00~300 ng/mL.

3 Test Results

For the rats administrated intragastricly 10 mg/kg of the test preparation, lutein was not detected in plasma (the content of lutein was reduced by gastric acid, and was below the minimum detectable concentration limit).

For the rats administrated orally 10 mg/kg of the test preparation, the concentration of lutein in plasma is shown in Table 2.

TABLE 2

Plasma concentration of lutein after oral administration of
10 mg/kg of test preparation 1 in rats (ng/mL)

| Time/h | 1 | 2 | 3 | 4 | Average | Standard deviation |
|---|---|---|---|---|---|---|
| 0.25 | 3.96 | BLQ | BLQ | BLQ | 0.99 | 1.98 |
| 0.5 | 3.33 | 13.2 | 3.22 | 4.36 | 6.03 | 4.81 |
| 1 | 15.8 | 46.4 | 5.78 | 15.7 | 20.9 | 17.6 |
| 2 | 12.3 | 52.2 | 8.66 | 12.5 | 21.4 | 20.6 |
| 3 | 9.13 | 38.3 | 8.33 | 6.81 | 15.6 | 15.1 |
| 5 | 6.82 | 13.8 | 7.04 | 10.5 | 9.54 | 3.30 |
| 7 | 6.25 | 23.4 | 8.39 | 9.69 | 11.9 | 7.8 |
| 10 | 4.90 | 7.29 | BLQ | 5.51 | 4.43 | 3.12 |
| 24 | BLQ | 3.98 | BLQ | BLQ | 1.00 | 1.99 |

As can be known from the results that, gastric acid has a certain destructive effect on the stability of lutein/lutein ester and reduces its bioavailability. Increase of the absorption of lutein/lutein ester by oral mucosa is an effective way to improve its bioavailability.

The invention claimed is:

1. A composition containing lutein/lutein ester, wherein the composition comprises lutein/lutein ester and beta-carotene and pharmaceutically acceptable carriers, the weight ratio of lutein/lutein ester to beta-carotene is 1.5-10:1, the composition comprises the following components by weight:

| | |
|---|---|
| lutein/lutein ester | 0.5-25% |
| cyclodextrin | 4.5-45% |
| acidity regulator | 3-10% |
| loose agent | 3-15% |
| calcium carbonate | 0-5% |
| lactose | 10-25% |
| maltodextrin | 5-25% |
| alditol | 5-20% |
| beta-carotene | 0.1-25% |
| sugar powder | 5-30% |
| fruit powder | 12-30% |
| magnesium stearate | 0.5-1.5%, | and
the composition is orally disintegrating tablet,
the acidity regulator is one or more selected from the group consisting of citric acid, malic acid, fumaric acid, lactic acid and tartaric acid;
the loose agent is one or more selected from the group consisting of soda, baking soda, calcium carbonate and magnesium carbonate;
the sugar powder is one or more selected from the group consisting of white granulated sugar powder, fructose powder and glucose powder;
the fruit powder is one or more of the darker fruit powders selected from the group consisting of blueberry powder, black currant powder, cranberry powder, tomato powder, grape powder and mulberry powder; and
the alditol is one or more selected from the group consisting of sorbitol, mannitol, xylitol, and erythritol.

2. The composition containing lutein/lutein ester according to claim 1, wherein
the composition comprises the following components by weight:

| | |
|---|---|
| lutein/lutein ester | 1.5-2% |
| cyclodextrin | 9-10% |
| acidity regulator | 5-6% |
| loose agent | 7-8% |
| calcium carbonate | 0-1% |
| lactose | 13-15% |
| maltodextrin | 12-15% |
| alditol | 10-14% |
| beta-carotene | 1-2% |
| sugar powder | 14-15% |
| fruit powder | 17-22% |
| magnesium stearate | 1-1.5%. |

3. A method for treating ocular diseases or for providing ocular health care, comprising administering to a subject in need thereof an effective amount of the composition according to claim 1.

4. The method according to claim 3, wherein
the ocular diseases comprise dizziness, eye pain, weak dark adaptation, blurred vision, photophobia, dry eyes, blink, myopia or macular degeneration of retina.

* * * * *